(12) United States Patent
Datta et al.

(10) Patent No.: US 8,759,515 B2
(45) Date of Patent: Jun. 24, 2014

(54) PROCESS FOR THE PREPARATION OF TENOFOVIR DISOPROXIL FUMARATE

(75) Inventors: Debashish Datta, Hyderabad (IN); Siva Rama Prasad Vellanki, Hyderabad (IN); Arabinda Sahu, Hyderabad (IN); Raja Babu Balusu, Hyderabad (IN); Mastan Rao Ravi, Hyderabad (IN); Hari Babu Nandipati, Hyderabad (IN); Shankar Rama, Hyderabad (IN); Lakshmana Rao Vadali, Hyderabad (IN); Srikanth Sarat Chandra Gorantla, Hyderabad (IN); Srinivasa Rao Dasari, Hyderabad (IN); Nagaraju Mittapelly, Hyderabad (IN)

(73) Assignee: Mylan Laboratories Limited, Hyderabad (IN)

( * ) Notice: Subject to any disclaimer, the term of this patent is extended or adjusted under 35 U.S.C. 154(b) by 0 days.

(21) Appl. No.: 13/583,951

(22) PCT Filed: Mar. 11, 2011

(86) PCT No.: PCT/IN2011/000164
§ 371 (c)(1),
(2), (4) Date: Sep. 11, 2012

(87) PCT Pub. No.: WO2011/111074
PCT Pub. Date: Sep. 15, 2011

(65) Prior Publication Data
US 2013/0005969 A1    Jan. 3, 2013

(30) Foreign Application Priority Data

Mar. 11, 2010    (IN) .............................. 637/CHE/2010
Apr. 15, 2010    (IN) ............................ 1050/CHE/2010

(51) Int. Cl.
*C07F 9/40*    (2006.01)
*C07D 473/34*    (2006.01)

(52) U.S. Cl.
USPC .......................................................... 544/244

(58) Field of Classification Search
USPC .......................................................... 544/244
See application file for complete search history.

(56) References Cited

U.S. PATENT DOCUMENTS 5,733,788 A  *  3/1998  Bischofberger ............... 436/98
2010/0216822 A1 *  8/2010  Yuan .......................... 514/263.4

FOREIGN PATENT DOCUMENTS

WO    WO 2010/007392 A2  *  1/2008

OTHER PUBLICATIONS

Bruice, Organic Chemistry, 6th ed. (2010) Prentice Hall.*
Reichardt, Solvents and Solvent Effects in Organic Chemistry, 3rd ed. (2003) Wiley-VCH.*

* cited by examiner

*Primary Examiner* — Golam M M Shameem
*Assistant Examiner* — Laura Daniel
(74) *Attorney, Agent, or Firm* — Ladas & Parry LLP

(57) ABSTRACT

The present invention relates to an improved process for the preparation of Tenofovir Disoproxil and its pharmaceutically acceptable salts comprising the steps of: a) esterifying Tenofovir with chloromethyl isopropyl carbonate in presence of a base, phase transfer catalyst and optionally dehydrating agent, in a suitable solvent; b) optionally purifying Tenofovir Disoproxil; and c) converting of Tenofovir Disoproxil into its pharmaceutically acceptable salts. The present invention further relates to a process for the preparation of Tenofovir by reacting 1-(6-amino-purin-9-yl)-propan-2-ol with toluene-4-sulfonic acid diethoxy phosphoryl methyl ester in presence of a base in a non-polar solvent medium followed by hydrolysis.

8 Claims, No Drawings

PROCESS FOR THE PREPARATION OF TENOFOVIR DISOPROXIL FUMARATE

This application claims priority to Indian patent applications 637/CHE/2010 filed on Mar. 11, 2010; 1050/CHE/2010 filed on Apr. 15, 2010; the contents of which are incorporated by reference in their entirety.

FIELD OF THE INVENTION

The present invention relates to an improved process for the preparation of Tenofovir Disoproxil and its pharmaceutically acceptable salts.

BACKGROUND OF THE INVENTION

Tenofovir Disoproxil is chemically known as 9-[-2-(R)-[[bis[[(isopropoxycarbonyl)oxy]methoxy]phosphinoyl]methoxy]propyl]-adenine, having the following structural formula-I.

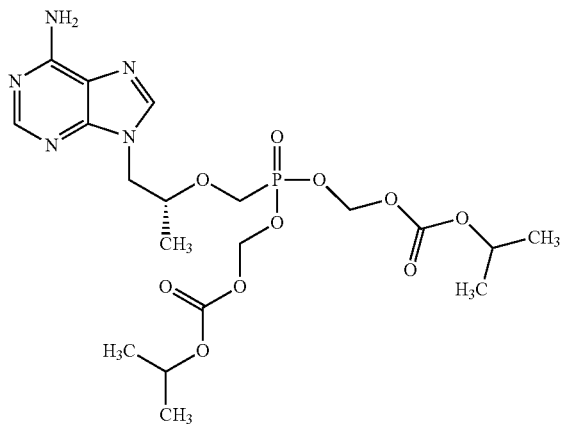

Formula-I

Tenofovir is a highly potent antiviral agent, particularly for the therapy or prophylaxis of retroviral infections and belongs to a class of drugs called Nucleotide Reverse Transcriptase Inhibitors (NRTI) which blocks reverse transcriptase an enzyme crucial to viral production in HIV-infected people.

Tenofovir Disoproxil and its pharmaceutically acceptable salts were first disclosed in U.S. Pat. No. 5,922,695. This patent discloses the preparation of Tenofovir Disoproxil by the esterification of Tenofovir with chloromethyl isopropyl carbonate using 1-methyl-2-pyrrolidinone and triethylamine. In this patent Tenofovir Disoproxil is converted into its Fumarate salt without isolation.

PCT Publication WO 2008007392 discloses process for the preparation of Tenofovir Disoproxil fumarate, wherein the isolated crystalline Tenofovir Disoproxil is converted into fumarate salt.

Tenofovir Disoproxil processes in the prior art are similar to process disclosed in product patent U.S. Pat. No. 5,922,695. According to the prior art processes, Tenofovir Disoproxil fumarate obtained is having low yields and also show the presence of impurities such as dimers.

Thus the present invention provides an improved process for the preparation of Tenofovir Disoproxil and its pharmaceutically acceptable salts with improved yield and quality.

OBJECT AND SUMMARY OF THE INVENTION

The principle object of the present invention is to provide an improved process for the preparation of Tenofovir Disoproxil and its pharmaceutically acceptable salts.

One aspect of the present invention provides, an improved process for the preparation of Tenofovir disoproxil comprising the steps of: a) esterifying Tenofovir with chloromethyl isopropyl carbonate in presence of a base, phase transfer catalyst and optionally dehydrating agent, in a suitable solvent; b) optionally purifying Tenofovir Disoproxil; and c) converting Tenofovir Disoproxil into its pharmaceutically acceptable salts.

Another aspect of the present invention provides, an improved process for the preparation of Tenofovir by reacting 1-(6-amino-purin-9-yl)-propan-2-ol with toluene-4-sulfonic acid diethoxy phosphoryl methyl ester in presence of base in a non-polar solvent medium followed by hydrolysis to yield Tenofovir

DETAILED DESCRIPTION OF THE INVENTION

The present invention relates to an improved process for the preparation of Tenofovir Disoproxil and its pharmaceutically acceptable salts comprising the steps of: a) esterifying Tenofovir with chloromethyl isopropyl carbonate in presence of a base, phase transfer catalyst optionally dehydrating agent, in a suitable solvent; b) optionally purifying Tenofovir Disoproxil; and c) converting of Tenofovir Disoproxil into, its pharmaceutically acceptable salts. The present invention further relates to a process for the preparation of Tenofovir by reacting 1-(6-amino-purin-9-yl)-propan-2-ol with toluene-4-sulfonic acid diethoxy phosphoryl methyl ester in presence of a base in a non-polar solvent medium followed by hydrolysis.

In one aspect, present invention provides, process for the preparation of Tenofovir disoproxil and its pharmaceutically acceptable salts comprising the steps of:
a) esterifying Tenofovir with chloromethyl isopropyl carbonate in presence of a base, phase transfer catalyst optionally dehydrating agent, in a suitable solvent;
b) optionally purifying Tenofovir Disoproxil; and
c) converting of Tenofovir Disoproxil into its pharmaceutically acceptable salts.

In one embodiment of the present invention, esterification of Tenofovir is carried out in presence of base and phase transfer catalyst, wherein base is selected from organic amine like trialkyl amine such as triethylamine, diisopropyl ethyl amine, preferably triethylamine; and phase transfer catalyst is selected from tertramethyl ammonium bromide, tetrabutyl ammonium bromide, methyl triethyl ammonium bromide, benzyl trimethyl ammonium bromide, benzyl triethyl ammonium bromide, molecular sieves and crown ethers; preferably tetrabutyl ammonium bromide.

In another embodiment of the present invention, esterification of Tenofovir is carried out optionally in presence of dehydrating agent. The dehydrating agent is selected from silylated dehydrating agent such as trialkylsilylhalides, bis (trimethylsilyl)acetamide (BSA) and hexamethyldisilazane (HMDS), preferably trialkyl silyl halides, more preferably trimethyl silyl chloride.

In another embodiment of the present invention, esterification of Tenofovir is carried out in a solvent selected from Acetonitrile, dimethyl formamide, N-Methyl pyrrolidine, cyclohexane, ethyl acetate, isopropyl acetate, n-heptane, isopropyl alcohol and water or mixtures thereof, preferably N-methyl pyrrolidine.

In another embodiment of the present invention, after esterification reaction of Tenofovir, reaction mass is treated with chilled water to yield Tenofovir Disoproxil as its chloromethyl isopropyl carbonate solvate.

In one more embodiment of the present invention, Tenofovir is dehydrated before esterfying with chloromethyl isopropyl carbonate. The dehydration is carried out by azeotropic distillation.

In one more embodiment of the present invention, dehydration and esterification of Tenofovir is carried out in-situ.

In one more embodiment of the present invention, Tenofovir disoproxil is optionally recrystallized in ester solvents such as ethyl acetate.

In another embodiment of the present invention, Tenofovir Disoproxil is converted into its pharmaceutically acceptable salts, preferably fumarate salt by the conventional methods.

During the esterification reaction it has been observed that due to prolonged heating of the reaction mass product starts degrading resulting impurities such as monoester. In view of this observation it is important to complete the esterification reaction in minimum possible time. Probably the esterification reaction takes place through the formation of triethyl amine salt of Tenofovir. The triethyl amine slat of Tenofovir is very limited solubility in the reaction media resulting in the formation of heterogeneous reaction system. We have observed that addition of phase transfer catalyst such as tetra butyl ammonium bromide, crown ether etc., improved the rate of reaction.

According to the present invention, by using the phase transfer catalyst along with dehydrating agents the yield of the Tenofovir Disoproxil and its pharmaceutically acceptable salts is increased from 60 to 85%. The dimer impurity formed by the prior art processes is minimized by using this invention.

According to the present invention, Tenofovir base is suspended in a solvent selected from acetonitrile, toluene, xylene, cyclohexane and methylene dichloride and a base selected from triethylamine and diisopropyl amine. The suspension is heated to high temperatures to remove water. Later solvent is concentrated under reduced pressure to obtain moisture free Tenofovir The obtained anhydrous Tenofovir is reacted with chloromethyl isopropyl carbonate using a base and a phase transfer catalyst in presence of a solvent. The base employed for the esterification step is selected from triethylamine and diisopropyl amine. And phase transfer catalyst is selected from tertramethyl ammonium bromide, tetrabutyl ammonium bromide, methyl triethyl ammonium bromide, benzyl trimethyl ammonium bromide, benzyl triethyl ammonium bromide, molecular sieves and crown ethers. Phase transfer catalyst employed in this reaction is about 1-3 moles ratio with respect to tenofovir. Esterification reaction is carried out optionally in the presence of dehydration agent such as trialkylsilylhalides, bis(trimethylsily)acetamide (BSA) and hexamethyldisilazane (HMDS), preferably trialkyl silyl halides, more preferably trimethyl silyl chloride.

The said reaction is carried out in a solvent selected from Acetonitrile, dimethyl formamide, N-Methyl pyrrolidine, cyclohexane, ethyl acetate, isopropyl acetate, n-heptane, isopropyl alcohol and water or mixtures thereof, preferably N-methyl pyrrolidine. Esterification can be carried out at 25-80° C. preferably 51-54° C. for a time period of 5-15 hrs preferably 5-7 hrs. The yield of the Tenofovir Disoproxil and its pharmaceutically acceptable salts has increased from 60 to 85%.

In another aspect, the present invention provides, an improved process for the preparation of Tenofovir by reacting 1-(6-amino-purin-9-yl)-propan-2-ol with toluene-4-sulfonic acid diethoxy phosphoryl methyl ester in presence of a base in a non-polar solvent medium followed by hydrolysis.

In one embodiment, condensation of 1-(6-amino-purin-9-yl)-propan-2-ol with toluene-4-sulfonic acid diethoxy phosphoryl methyl ester is carried out in presence of a base wherein, base is selected from alkaline metal alkoxide such as magnesium-tert-butaoxide, potassium-tert-butaoxide, preferably magnesium-tert-butaoxide.

In one more embodiment, condensation of 1-(6-amino-purin-9-yl)-propan-2-ol with toluene-4-sulfonic acid diethoxy phosphoryl methyl ester is carried out in a non-polar solvent optionally in presence of polar solvent. The non-polar solvent is selected from cyclohexane, toluene, benzene, 1,4-dioxane and chloroform, preferably toluene. The polar solvent is selected from dimethyl formamide or N-methyl pyrrolidone.

In prior art processes, reaction of 9-R-(2-Hydroxypropyl) adenine with toluene-4-sulfonic acid diethoxy phosphoryl methyl ester is carried out in presence of a base such as magnesium ter-butoxide in high boiling point solvents such as dimethyl formamide. In the workup process, removal of DMF becomes cumbersome and also impurities are formed in the product.

According to the present invention, Tenofovir base synthesis involves reaction of 9-R-(2-Hydroxypropyl) adenine with toluene-4-sulfonic acid diethoxy phosphoryl methyl ester in presence of a base such as magnesium ter-butoxide in a non polar solvent, followed by hydrolysis with aq. HBr. The non-polar solvent used in the condensation step is selected from cyclohexane, toluene, benzene and 1,4-dioxane, preferably toluene. Reaction is carried out in presence of solvent such as dimethyl formamide or N-methyl pyrrolidone in a volume ratio ranging from 0.10 to 0.30 volumes (w/w with respect to adenine derivative compound). Reaction is carried out at 50-80° C. preferably 74-76° C. for about 5-6 hrs. After completion of the reaction, acetic acid is added and reacted with aq. Hydrobromic acid and maintained at 90-95° C. to yield Tenofovir.

Process for the preparation of Tenofovir disoproxil fumarate is schematically represented in scheme-1.

Scheme-1

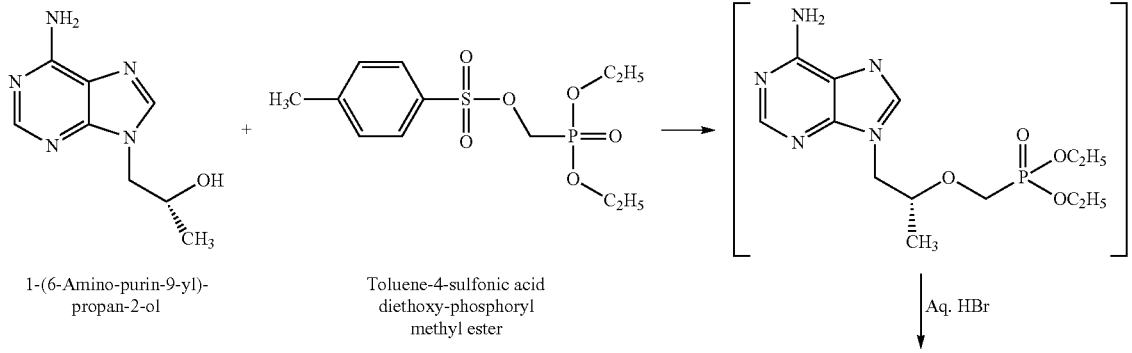

1-(6-Amino-purin-9-yl)-propan-2-ol

Toluene-4-sulfonic acid diethoxy-phosphoryl methyl ester

Aq. HBr

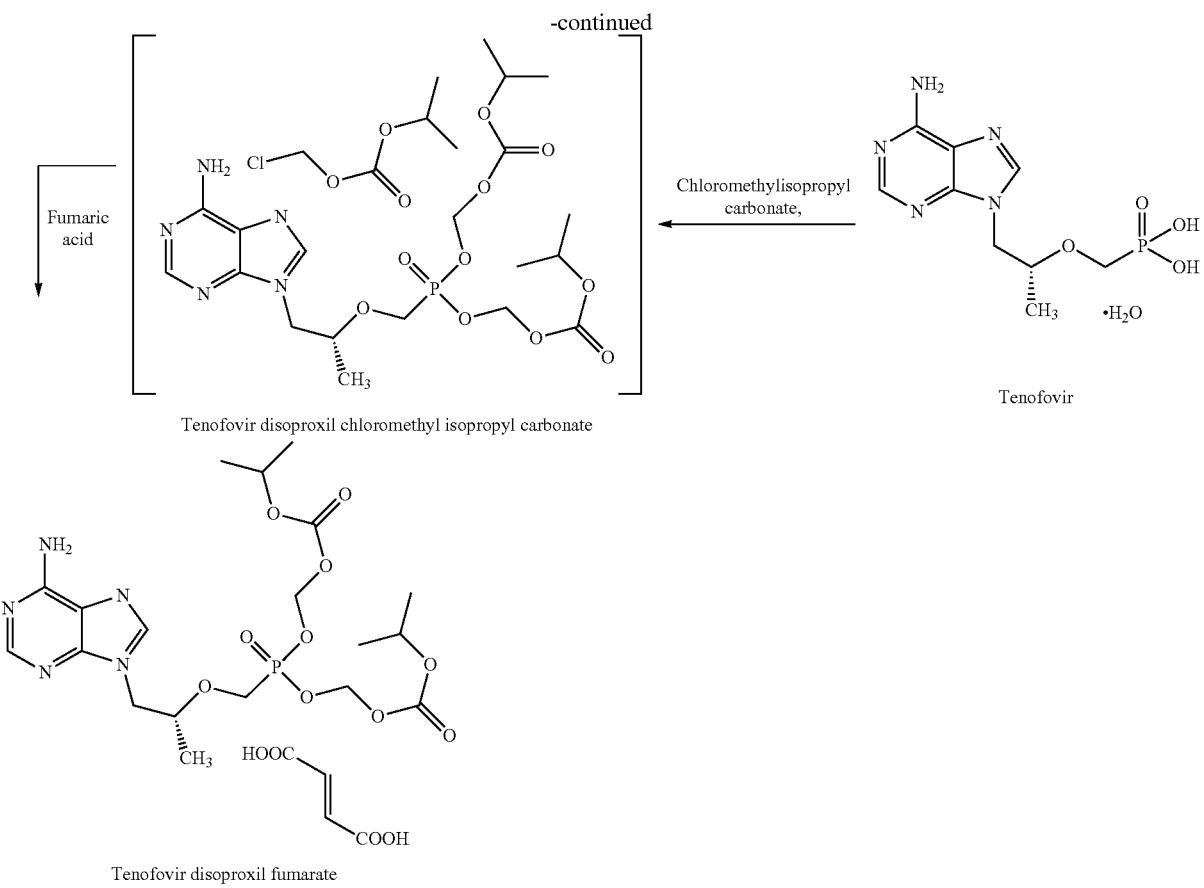

The present invention also provides a pharmaceutical composition that includes a therapeutically effective amount of Tenofovir Disoproxil and its pharmaceutically acceptable salts prepared according to the process of the present invention and one or more pharmaceutically acceptable carriers, excipients or diluents.

According to the present invention, the pharmaceutical composition comprising Tenofovir Diisoproxil or pharmaceutically acceptable salts along with one or more pharmaceutically acceptable carriers of this invention may further be formulated as solid oral dosage forms such as, but not limited to, powders, granules, pellets, tablets, and capsules; liquid oral dosage forms such as but not limited to syrups, suspensions, dispersions, and emulsions, and injectable preparations such as but not limited to solutions, dispersions, and freeze dried compositions. Formulations may be in the form of immediate release, delayed release or modified release. The compositions may be prepared by direct blending, dry granulation, or wet granulation or by extrusion and spheronization. Compositions may be presented as uncoated, film coated, sugar coated, powder coated, enteric coated or modified release coated. Compositions of the present invention may further comprise one or more pharmaceutically acceptable excipients.

The following examples are provided for illustrative purposes only and are not intended to limit the scope of the invention in any way.

Example 1

Process for the Preparation of Tenofovir Disoproxil Fumarate

Toluene (500 ml) was added to the Tenofovir (100 gm) and stirred at room temperature. To this triethylamine (66.31 gm) was added, temperature was raised to 90° C. and water was collected by azeotropic distillation at 110° C. Toluene was completely distilled under vacuum at same temperature. The reaction mixture was cooled to room temperature and to this a mixture of N-methyl pyrrolidine (300 gm), triethylamine (66.31 gm), Tetrabutyl ammonium bromide (52.8 gm) and trimethyl silyl chloride (17.8 gm) were added. The above reaction mixture was heated to 50-55° C. and was added slowly chloromethyl isopropyl carbonate (CMIC) and maintained the reaction mixture at 50-55° C. for 5 hrs. (Qualitative HPLC analysis shows about 85% product formation). The above reaction mixture was cooled to room temperature and filtered. The filtrate was added to DM water at 5-10° C. and extract with dichloromethane. The combined dichloromethane layer was concentrated under vacuum and the crude was Co-distilled with cyclohexane and this crude was taken into isopropyl alcohol (1000 ml). To this fumaric acid (38 gm) was added and temperature was raised to 50° C. The reaction mixture was filtered and filtrate was cooled to 5-10° C. The obtained solid was filtered and washed with isopropyl alcohol. The compound was dried under vacuum to yield Tenofovir Disoproxil fumarate (140 gm).

Example-2

Preparation of Tenofovir

N-methyl-2-pyrrolidone (25 gm) was taken along with toluene (150 gm) into a reaction vessel. 1-(6-amino-purin-9-yl)-propan-2-ol (100 gm); toluene-4-sulfonic acid diethoxy phosphoryl methyl ester (200 gm) and magnesium ter-butoxide (71.2 gm) were also taken at 25-35° C. Temperature was raised to 74-75° C. and maintained for 5-6 hrs. After completion of reaction, acetic acid (60 gm) was added and maintained for 1 hr. Later aq.HBr (332 gm) was taken and heated to 90-95° C. After reaction completion, salts were filtered and filtrate was subjected to washings with water and extracted into methylene dichloride. Later pH was adjusted using CS lye below 10° C. Tenofovir product was isolated using acetone.

Yield: 110 gm.

Example 3

Preparation of Tenofovir Disoproxil (R)-9-[2-(phosphonomethoxy)propyl]adenine (25 gm), triethyl amine (25 ml) and cyclohexane (200 ml) were combined and heated to remove water and the solvent was distilled off under vacuum. The reaction mass was cooled to room temperature N-methyl pyrrolidinone (55 ml), triethyl amine (25 ml) and tetra butyl ammonium bromide (54 gms) were added to the reaction mixture. The reaction mass was heated to 50-60° C. and chloromethyl isopropyl carbonate (65 gm) was added and maintained for 4-8 hrs at 50-60° C. and then cooled to 0° C. The reaction mass was diluted with chilled water or ice and precipitated solid product was filtered. The mother liquor was extracted with methylene chloride (150 ml). The methylene chloride layer was washed with water (200 ml). The filtered solid and the methylene chloride layer were combined and washed with water and the solvent was distilled under vacuum. Ethyl acetate was charged to the precipitated solid. The reaction mass was then cooled to 0-5° C. and maintained for 6 hrs. The solid was filtered and dried to produce Tenofovir disoproxil (45 gm).

We claim:

1. A process for the preparation of Tenofovir Disoproxil and its pharmaceutically acceptable salts thereof comprising the steps of:

a) esterifying Tenofovir with chloromethyl isopropyl carbonate in presence of a base, phase transfer catalyst and a silylating agent as a dehydrating agent, in a solvent;

b) optionally purifying the resulting Tenofovir Disoproxil; and c) optionally converting the Tenofovir Disoproxil into the desired pharmaceutically acceptable salt.

2. The process according to claim 1, wherein the phase transfer catalyst is selected from the group consisting of tetramethyl ammonium bromide, tetrabutyl ammonium bromide, methyl triethyl ammonium bromide, benzyl trimethyl ammonium bromide, benzyl triethyl ammonium bromide, molecular sieves and crown ethers.

3. The process according to claim 1, wherein the base is a trialkylamine.

4. The process according to claim 3, wherein the trialkylamine is selected from triethylamine and diisopropylethylamine.

5. The process according to claim 1, wherein the solvent is selected from the group consisting of acetonitrile, dimethyl formamide, N-methyl pyrrolidine, cyclohexane, ethyl acetate, isopropyl acetate, n-heptane, isopropyl alcohol, water and mixtures thereof.

6. The process according to claim 1, wherein the pharmaceutically acceptable salt is a fumarate salt.

7. A process for the preparation of Tenofovir Disoproxil fumarate comprising the steps of:

a) esterifying Tenofovir with chloromethyl isopropyl carbonate in the presence of the base triethylamine, the phase transfer catalyst tetrabutyl ammonium bromide and the dehydrating agent bis(trimethylsilyl) acetamide, in N-Methyl pyrrolidone as a solvent;

b) optionally purifying the resulting Tenofovir Disoproxil; and c) converting the Tenofovir Disoproxil into a fumarate salt.

8. A process for the preparation of Tenofovir Disoproxil comprising the steps of reacting 1-(6-amino-purin-9-yl)-propan-2-ol with toluene-4-sulfonic acid diethoxy phosphoryl methyl ester in the presence of a base in a non-polar solvent medium followed by hydrolysis to yield Tenofovir, which is further converted to Tenofovir Disoproxil via a process according to claim 7.

* * * * *